United States Patent [19]

Drews

[11] Patent Number: 4,764,170
[45] Date of Patent: Aug. 16, 1988

[54] APPARATUS FOR PLUGGING AN INTRAOCULAR LENS HOLE

[76] Inventor: Robert C. Drews, 211 N. Meramac Ave., Clayton, Mo. 63105

[21] Appl. No.: 2,381

[22] Filed: Jan. 12, 1987

[51] Int. Cl.$^4$ .......................... A61F 2/16; A61B 17/00
[52] U.S. Cl. .................................. 623/6; 128/303 R
[58] Field of Search ........................................ 623/4–6; 604/893–895, 8

[56] References Cited

U.S. PATENT DOCUMENTS

| | | | |
|---|---|---|---|
| 2,810,134 | 10/1957 | Radin | 623/4 |
| 3,949,750 | 4/1976 | Freeman | 604/893 |
| 4,573,998 | 3/1986 | Mazzocco | 623/6 |
| 4,678,469 | 7/1987 | Kelman | 623/6 |

Primary Examiner—Ronald L. Frinks
Attorney, Agent, or Firm—Hugh D. Jaeger

[57] ABSTRACT

A hole plug for an intraocular lens for insertion into a positioning hole in a posterior chamber lens for reduction of glare, flare, reflection, radial lines or circular disks. The lens plug is opaque. The plug stops light from entering into the positioning hole. Cross-action forceps or other instruments are utilized through an incision to provide support for the optic, as well as pushing the hole plug into the positioning hole. The forceps may include a cavity to hold the plug during the insertion operation. The hole plug can also have an opaque skirt extending beyond the lens in an instance of a lens which does not cover the eye pupil.

6 Claims, 7 Drawing Sheets

APPARATUS FOR PLUGGING AN INTRAOCULAR LENS HOLE

BACKGROUND OF THE INVENTION

1. Field of the Invention

The present invention pertains to a hole plug for an intraocular lens, and more importantly, pertains to a hole plug with a skirt, as well as cross-action forceps for inserting the hole plug through an incision in the eye.

2. Description of the Prior Art

Posterior chamber lenses are provided with an optional plurality of holes by the manufacture. For example, a posterior chamber lens can be manufactured with no positioning holes, two positioning holes, or four positioning holes. The number of positioning holes is basically the ophthalmologist's preference.

The positioning holes unfortunately allow light to pass through the positioning holes, which in some patients causes glare, radial lines, flare or circular discs in the posterior chamber lens whenever the hole becomes exposed in the pupil. Further, fibrosis can cause the pupil's center position to migrate off center to expose the positioning holes in the IOL causing unwanted light interference in the vision.

The present invention overcomes the disadvantages of the prior art by providing a positioning hole plug, as well as a method for inserting the positioning hole plug, and thereby minimizing if not eliminating the above prior art problems.

SUMMARY OF THE INVENTION

The general purpose of the present invention is a intraocular lens hole plug for insertion into a positioning hole in a posterior chamber lens. The hole plug can be inserted through an incision with cross action forceps which provide support for the optic as well as including a cavity in the forceps to center and align the plug during insertion of the plug into the positioning hole.

According to one embodiment of the present invention, there is provided an opaque hole plug for insertion into a positioning hole in a posterior chamber lens. The opaque hole plug can also include a skirt for assisting in occlusion of light past the lens edge in the case of migration of the lens or pupil where the lens edge is exposed in the pupil. The hole plug and the hole plug with the skirt can be made of compatible materials to the lens, such as out of PMMA, HEMA, silicone, or any other like biocompatible material. The forceps include a lower section for supporting the posterior surface of intraocular lens and an upper section with a cavity for engaging with the top part of a hole plug and conforming to the surface of the lens. A plug ejector lever is also included in the upper forceps section. The forceps are small so as to be inserted through an incision in the eye.

Significant aspects and features of the present invention include an opaque or semi-opaque plug for insertion into a positioning hole in a posterior chamber lens for reduction and/or elimination of glare, flare, radial lines or circular discs.

Other significant aspects and features of the present invention is a hole plug with a skirt which overlaps the edge of the lens, for instance a lens which has experienced extreme migration.

Having thus described the principal embodiments of the present invention, it is a principal object hereof to provide a method and apparatus of an intraocular lens hole plug.

One object of the present invention is to provide an intraocular lens hole plug with or without a skirt.

Another object of the present invention is to provide a method of inserting a hole plug into an intraocular lens with cross-action forceps which are utilized through an incision in the eye.

DESCRIPTION OF THE PREFERRED EMBODIMENTS

Figure 1:
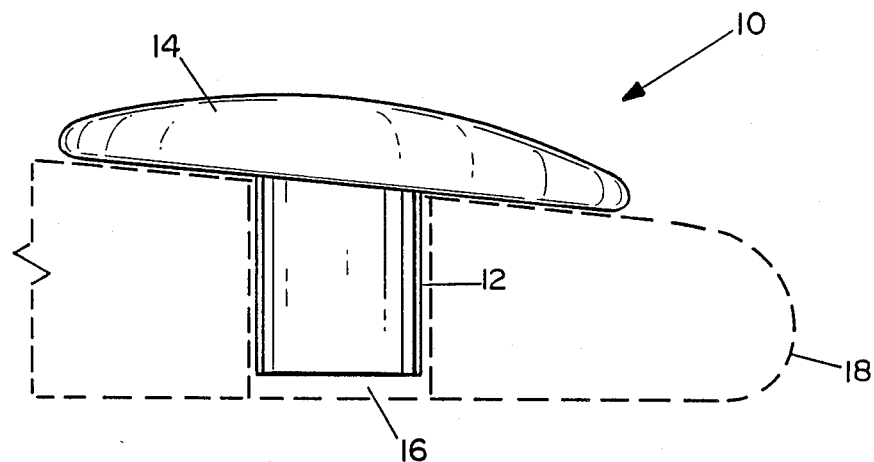
FIG. 1 illustrates a side view of an opaque hole plug.

FIG. 1 illustrates a side view of an intraocular lens hole plug 10, the present invention. The hole plug is sized to manufacturer specifications for positioning holes of a specific lens. The length of the hole plug 10 is such as to accommodate the internal length of the positioning hole. The head 14 of the hole plug 10 is positioned obliquely and integral to shaft 12 and is rounded and overlaps the diameter of the positioning hole when inserted. The shaft 12 frictionally engages into a positioning hole 16 in lens 18 shown in dashed lines. The hole plug 10 can be made of PMMA, HEMA, polyurethane silicone, or any other like biocompatible material which is acceptable to the IOL as well as the eye, and may be opaque.

Figure 2:
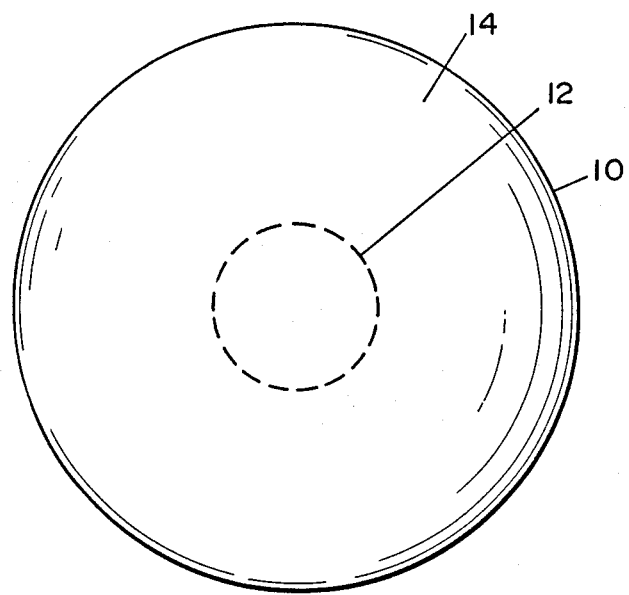
FIG. 2 illustrates a top view of FIG. 1.

FIG. 2 illustrates a top view of the lens hole plug 10 of FIG. 1 where all numerals correspond to those previously described.

Figure 3:
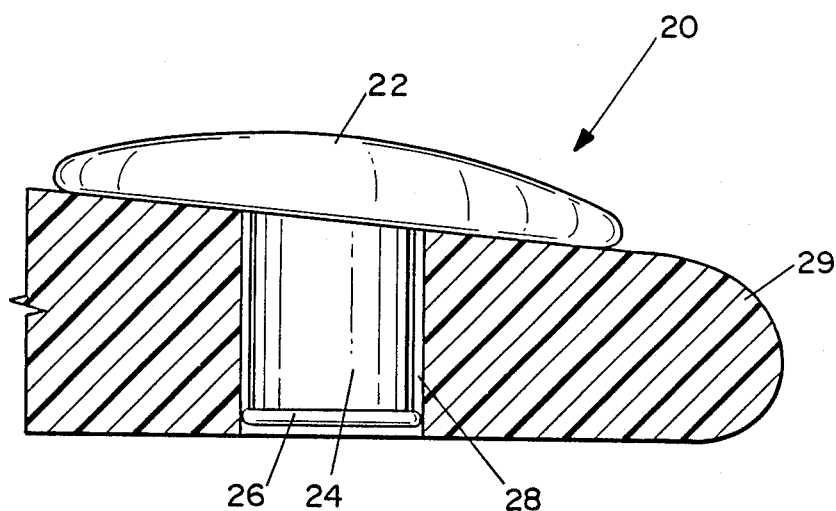
FIG. 3 illustrates an alternative embodiment of a lens plug of FIG. 1 including a shaft ring.

FIG. 3 illustrates an alternative embodiment of FIG. 1 including a lens hole plug 20 similar to lens hole plug 10, including an oval top head 22 positioned obliquely and integral to shaft 24. A rounded annular ring 26 positions around and about the lower portion of shaft 24 for frictional engagement within positioning hole 28 of lens 29 as illustrated in cross-section, allowing for an alternative method of frictional fixation of the lens hole plug 20 within the lens 29 which requires a lower degree of precision fitting between the mating shaft portion and hole portion of the lens hole plug 20 and positioning hole 28.

Figure 4:
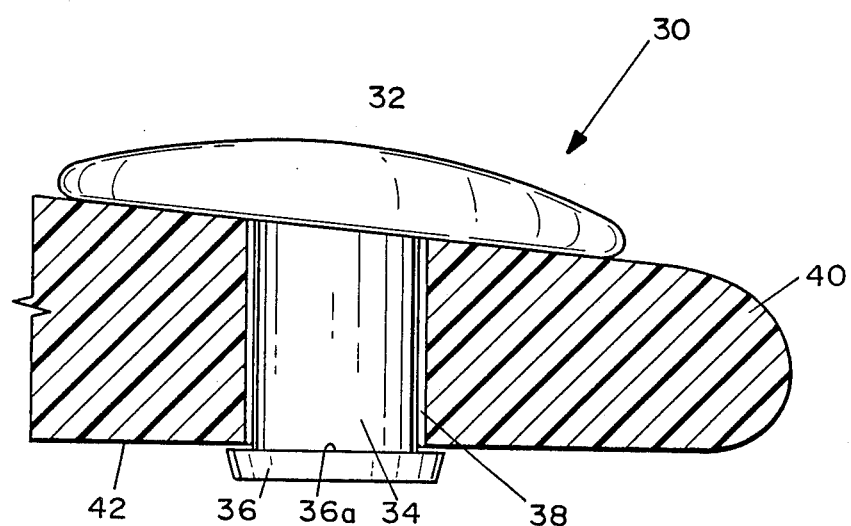
FIG. 4 illustrates an alternative embodiment of a lens plug of FIG. 1 including an angled securement ring.

FIG. 4 illustrates an alternative embodiment of FIG. 1 including a lens hole plug 30 similar to lens hole plug 10 including an oval top head 32 positioned obliquely and integral to shaft 34. An angled wall annular ring 36 positions around and about the lower portion of shaft 34 for a one way snap frictional engagement through hole 38 of lens 40 as illustrated in cross-section, allowing for an alternative positive method of frictional fixation and engagement of the lens hole plug 30 within the lens 40. Once the angled wall annular ring 36 passes by the bottom surface 42 of the lens 40, disengagement from the lens hole 38 is prevented when the upper portion 36a of the angled wall annular ring 36 engages against the bottom surface 42 surrounding hole 38.

Figure 5:
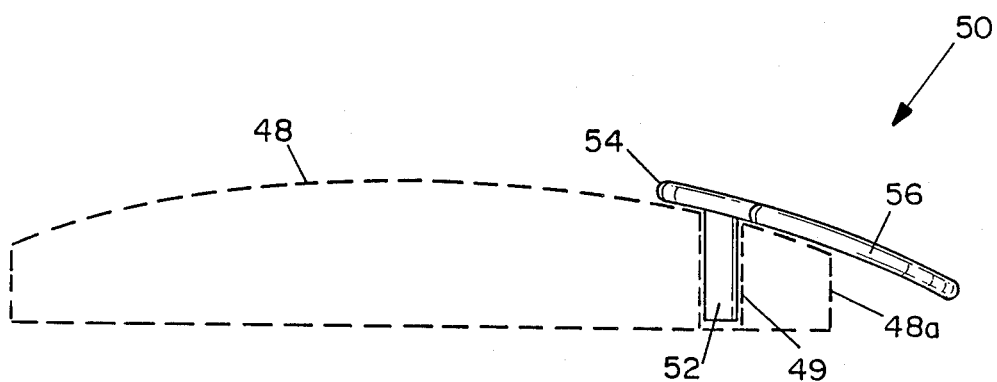
FIG. 5 illustrates a side view of an opaque hole plug with a skirt.

FIG. 5 illustrates an alternative embodiment of an opaque hole plug 50 including hole shaft 52, a rounded top portion 54 and a skirt 56 for extending over the edge of the lens. The hole plug 50 including skirt 56 can be made of the same materials as previously discussed with respect to FIGS. 1 and 2 and fits over the edge of an IOL optic 48 illustrated in dashed lines and occludes light from the lens edge 48a. Hole plug 52 is shown engaged in hole 49 of the optic 48.

Figure 6:
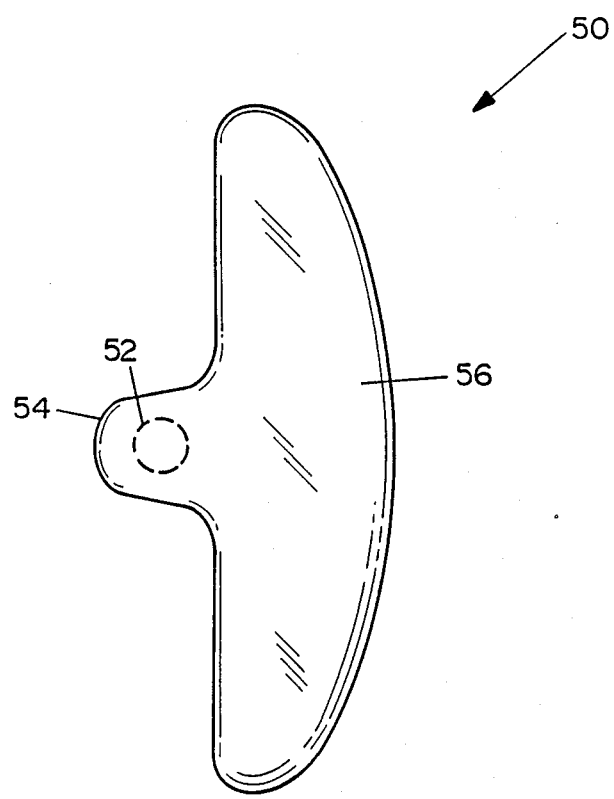
FIG. 6 illustrates a top view of FIG. 3.

FIG. 6 illustrates a top view of the hole plug 50 including the skirt 56. The skirt 56 is opaque as well as the hole plug area 52 which can also be opaque.

MODE OF OPERATION

Figure 7:
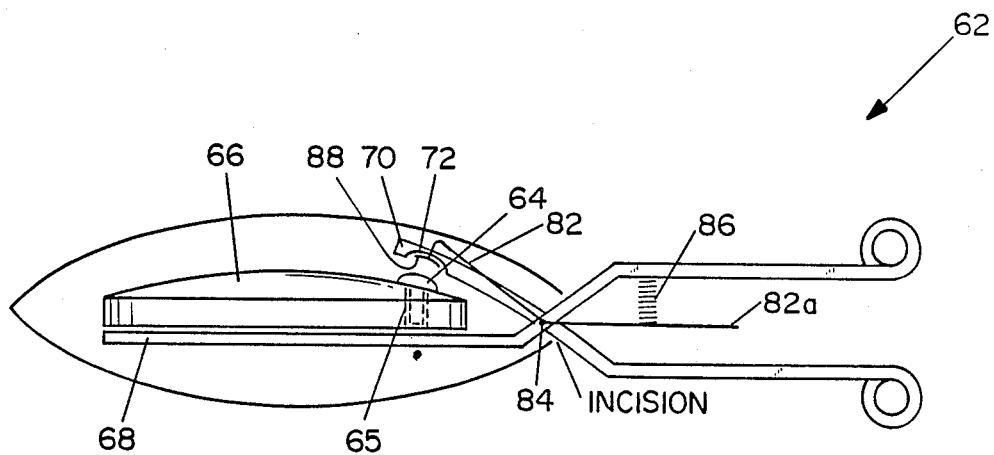
FIG. 7 illustrates the method of utilizing cross action forceps for insertion of an opaque hole plug into an intraocular lens.

FIG. 7 illustrates one method 60 of inserting the hole plug into a posterior chamber lens. In this specific example, a pair of cross-action forceps 62, are utilized to insert a hole plug 64 into a posterior chamber lens 66. The cross-action forceps include a lower member 68 which will conform to the posterior surface of the lens and a upper arm surface 70 with a cavity 72. The lower member 68 of cross-action forceps 62 can be a meniscus configuration, a plano configuration, or a convex configuration depending upon the particular style of posterior chamber lens. The upper arm surface 70, which includes cavity 72 in the cross-action forceps 62, will conform to the curvature of a convex posterior chamber lens surface. Configured cavity 72 is dimensioned appropriately to allow for a disengageable friction fit of the lens hole plug 64. The lens hole plug 64 is positioned in the cavity 72 prior to insertion of the forceps end and lens hole plug 64 through the wound. The plug is then positioned over the positioning hole 65 in the lens while at the same time positioning lower forceps member 68 beneath the lens 66. The handles are then squeezed, thus inserting the lens hole plug 64 into the positioning hole 65 of lens 66. A plug disengagement lever bar 82 pivots about an axis pin 84 through cross-action forceps 62. Disengagement lever bar end 82a is moved upwardly against spring 86 to disengage the hole plug 64 from cavity 72 by action of the configured cup shaped member against hole plug 64 should the hole plug 64 not disengage from the upper arm surface 70 subsequent to placement in the positioning hole 65. The cross-action forceps 62 are narrow enough to fit in through an incision in the eye for positioning and placement of the plug or plug with a skirt into a positioning hole.

The opaque skirt 56 of FIGS. 5 and 6 provides for blocking of light from a lens which is off center with respect to the pupil margin. The opaque skirt fills in a gap which would exist between an off center lens and the pupil. The opaque skirt solves this problem by blocking that specific area occluding the unobstructive transmission of light.

Figure 7A:
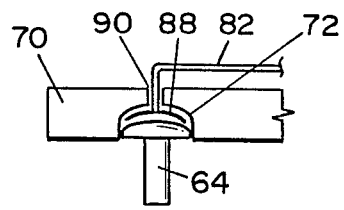
FIG. 7A illustrates a configured plug head cavity and ejector.

FIG. 7A illustrates a detailed view of the cup shaped member 88 in cavity 72. Plug disengagement lever bar 82 traverses through hole 90 and secures to cup shaped member 88 for engagement with the upper surface of the hole plug 64 to disengage the hole plug 64 from cavity 72.

Figure 8:
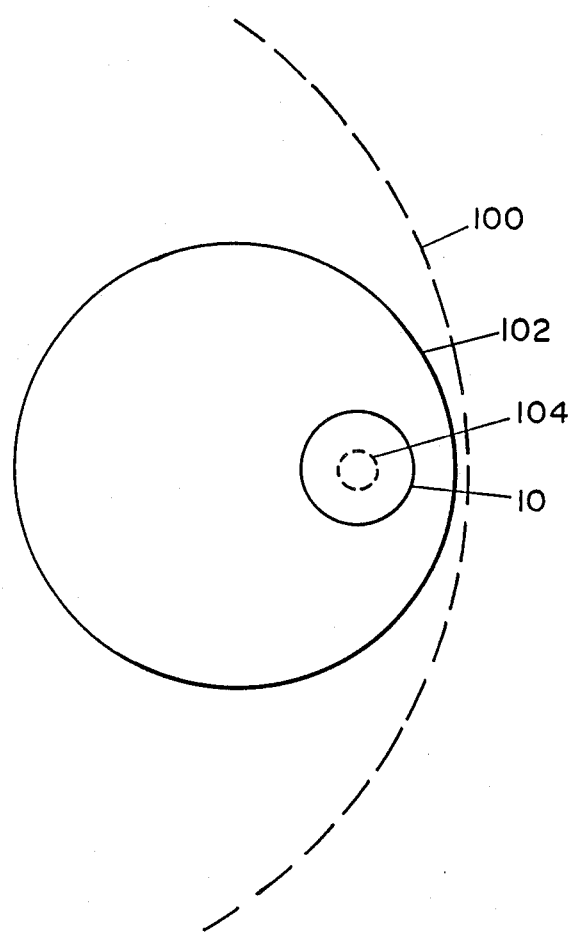
FIG. 8 illustrates an opaque hole plug inserted into an IOL.

FIG. 8 illustrates a hole plug 10 inserted into an IOL lens optic 100 where the optic 100 has migrated off center, and near to, but not into, the pupil 102 to allow transmission of light into the positioning hole 104 in the lens optic 100.

Figure 9:
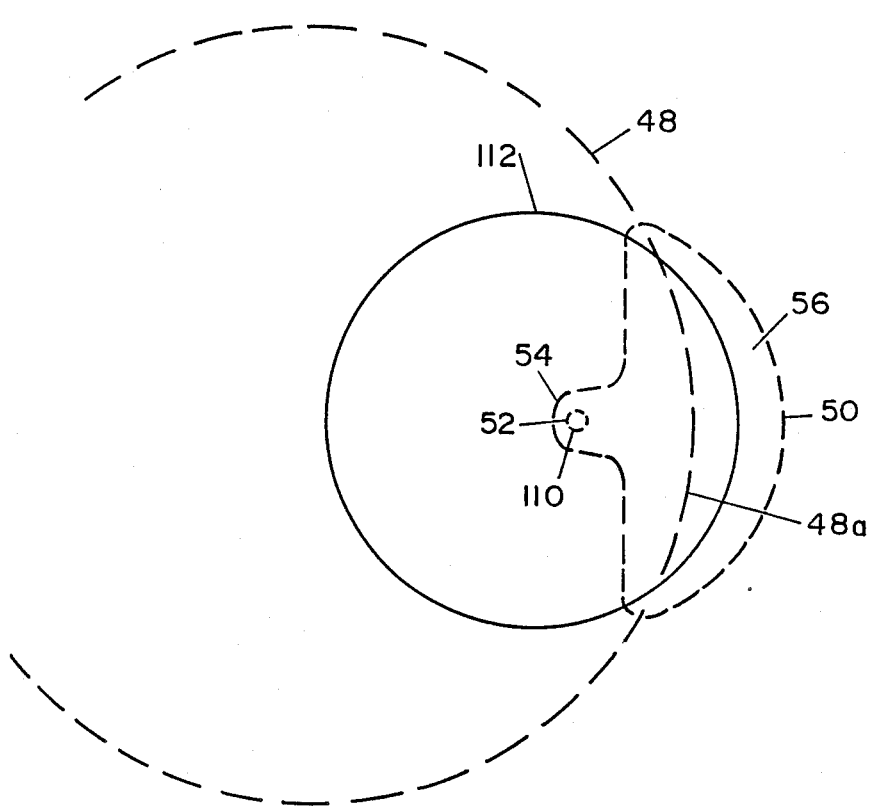
FIG. 9 illustrates an opaque skirted hole plug inserted into an IOL.

FIG. 9 illustrates a hole plug 50 inserted into hole 110 and overlying optic edge 48a in lens optic 48a where the lens optic edge 48 has migrated well into the pupil 112 exposing edge 48a to light. Skirt 56 overlies optic edge 48a to occlude light entry to the optic 48 through optic edge 48a.

Various modifications can be made to the present invention without departing from the apparent scope thereof. The hole plug can also be utilized in holes in anterior chamber lenses and iris clip lenses.

I claim:
1. Intraocular lens hole plug comprising:
   a. a shaft of a predetermined length and predetermined width, and having a configured bottom;
   b. a head secured to said shaft and rounded about a top surface and skirt means affixed about said head; and,
   c. said shaft and said head composed of a material which is compatible to the intraocular lens material, as well as biocompatible to the eye.
2. Plug of claim 1 wherein said material is PMMA.
3. Plug of claim 1 wherein said material is silicone rubber.
4. Plug of claim 1 wherein said material is polyurethane.
5. Plug of claim 1 wherein said skirt means is opaque.
6. Plug of claim 1 wherein said bottom is plano.

* * * * *